United States Patent [19]

Briner

[11] Patent Number: 5,521,317
[45] Date of Patent: May 28, 1996

[54] PROCESSES FOR THE PREPARATION OF PESTICIDES AND INTERMEDIATES

[75] Inventor: Paul H. Briner, Oxon, England

[73] Assignee: American Cyanamid Co., Madison, N.J.

[21] Appl. No.: 322,044

[22] Filed: Oct. 12, 1994

[30] Foreign Application Priority Data

Oct. 22, 1993 [EP] European Pat. Off. ............. 93308420

[51] Int. Cl.⁶ ................................................ C07D 277/56
[52] U.S. Cl. ................... 548/200; 544/406; 546/165; 548/127; 548/214; 549/487; 564/413; 564/414; 564/428
[58] Field of Search .................... 564/413, 414, 564/428; 546/165; 544/406; 548/127, 200, 214; 549/487

[56] References Cited

FOREIGN PATENT DOCUMENTS

| | | |
|---|---|---|
| 0023306 | 4/1981 | European Pat. Off. ...... C07D 215/08 |
| 0276177 | 7/1988 | European Pat. Off. ...... C07D 277/56 |
| 0280275 | 8/1988 | European Pat. Off. ...... C07D 275/02 |
| 097778 | 4/1993 | Japan . |
| 056788 | 3/1994 | Japan . |
| 355146 | 8/1961 | Switzerland . |

*Primary Examiner*—Richard L. Raymond
*Attorney, Agent, or Firm*—Charles F. Costello

[57] ABSTRACT

There is disclosed a process for the preparation of an indanylamine compound of general formula

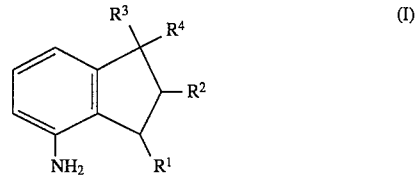

(I)

wherein $R^1$ represents an optionally substituted alkyl group, and $R^2$, $R^3$ and $R^4$ independently represent a hydrogen atom or an optionally substituted alkyl group, the process including the steps of hydrogenating a compound of general formula

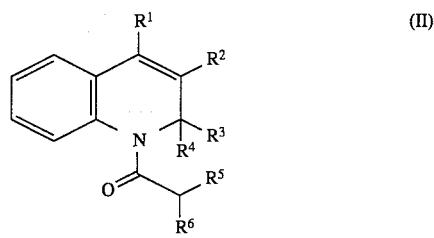

(II)

wherein $R^1$, $R^2$, $R^3$ and $R^4$ are as described above and $R^5$ and $R^6$ independently represent a halogen atom, a hydroxyl, nitro or cyano group, or an optionally substituted alkyl, alkoxy, alkoxycarbonyl, alkylcarboxy or alkylamino group provided that $R^5$ and $R^6$ represent different atoms or groups, and subsequent rearrangement and derivatization of the product thereof. Compounds of general formula I may be used to prepare preferred stereoisomers of fungicidal N-indanyl carboxamide compounds.

6 Claims, No Drawings

PROCESSES FOR THE PREPARATION OF PESTICIDES AND INTERMEDIATES

This invention relates to a process for the preparation of pesticides and intermediates. Particularly, although not exclusively, the invention relates to the predominant preparation of preferred stereoisomers of indanylamine compounds which may be used to predominantly prepare preferred stereoisomers of fungicidal N-indanyl carboxamide derivatives.

European Patent Application Number 0 280 275 (Mitsubishi Kasei Corporation) describes fungicidal N-indanyl carboxamide derivatives of general formula:

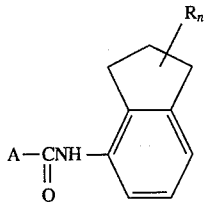

wherein R represents a lower alkyl group, n is an integer from 1 to 6 and A represents various optionally substituted heterocyclic groups.

Japanese Laid-Open Publication No. 92-54173 (Mitsubishi Kasei Corporation) discloses an optionally active N-indanylthiazole carboxamide having enhanced fungicidal activity and a process for the preparation thereof. The particular compound disclosed is 4-methyl-N-(3R-1,1,3-trimethylindan-4-yl)thiazole-5-carboxamide. The process for the preparation of the compound involves optically resolving 4-methyl-N-(1,1,3-trimethylindan-4-yl)thiazole-5-carboxamide using, for example, an optical isomer separating column. As a consequence of the process described, the yield of the preferred enantiomer may be relatively low.

This invention is based on the discovery of a novel process for the preparation of indanylamine compounds which may be used in the preparation of preferred stereoisomers of fungicidal N-indanyl carboxamide derivatives.

According to a first aspect of the present invention, there is provided a process for the preparation of an indanylamine compound of general formula

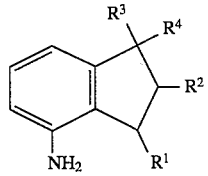

I wherein $R^1$ represents an optionally substituted alkyl group, and $R^2$, $R^3$ and $R^4$ independently represent a hydrogen atom or an optionally substituted alkyl group, the process including the steps of hydrogenating a compound of general formula

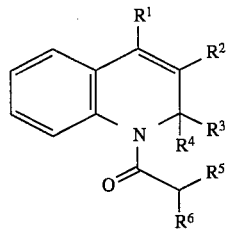

II wherein $R^1$, $R^2$, $R^3$ and $R^4$ are as described above and $R^5$ and $R^6$ independently represent a halogen atom, a hydroxyl, nitro or cyano group, or an optionally substituted alkyl, alkoxy, alkoxycarbonyl, alkylcarboxy or alkylamino group provided that $R^5$ and $R^6$ represent different atoms or groups, and subsequent rearrangement and derivatisation of the product thereof.

The process has been found to be advantageous in producing compounds of the general formula I in which a preferred stereoisomer of the compound may predominate. It is believed that this arises from the chiral nature of the group $R^5R^6CH-$ in the compound of general formula II. One configuration of the group $R^5R^6CH-$ suitably predominates in the compound of general formula II. Preferably, the compound of general formula II consists essentially of a single configuration of the group $R^5R^6CH-$.

Generally, when any moiety described herein comprises an alkyl group, this alkyl group may be linear or branched and may suitably contain 1 to 4 carbon atoms, suitable examples being methyl, ethyl and propyl. When any groups are designated as being optionally substituted, the substituent groups which are optionally present may be any of those customarily employed in the development of pesticidal compounds, and/or the modification of such compounds to influence their structure/activity, persistence, penetration or other property. In relation to moieties defined herein which comprise an optionally substituted alkyl or alkylene group, specific examples of such substituents include halogen, especially fluorine, chlorine or bromine atoms, and nitro, cyano, hydroxyl, $C_{1-4}$ alkoxy, $C_{1-4}$ haloalkoxy, $(C_{1-4}$ alkoxy)carbonyl groups, amino and $C_{1-4}$ alkylamino groups. It is preferred, however, that alkyl moieties are unsubstituted or halogen-substituted and that alkylene moieties are unsubstituted or only substituted by alkyl.

In the context of this specification, the term "predominant" (or like term) indicates greater than 50% and, more preferably, greater than 60%.

Preferably, $R^1$ represents an unsubstituted alkyl group. $R^1$ preferably represents a $C_{1-2}$ alkyl group. More preferably, $R^1$ represents a methyl group.

Preferably, $R^2$ represents a hydrogen atom or a $C_{1-2}$ alkyl group. More preferably, $R^2$ represents a hydrogen atom.

Preferably, $R^3$ and $R^4$ independently represent a hydrogen atom or a $C_{1-2}$ alkyl group. More preferably, $R^3$ and $R^4$ represent a $C_{1-2}$ alkyl group. Especially preferred is the case wherein $R^3$ and $R^4$ represent a methyl group.

Preferably, $R^5$ represents an optionally substituted $C_{1-6}$ alkyl group. More preferably, $R^5$ represents a $C_{1-4}$ alkyl group. Especially preferred is the case wherein $R^5$ represents a methyl group.

Preferably $R^6$ represents a halogen atom, a hydroxyl group or an optionally substituted alkoxy, alkoxycarbonyl or alkylcarboxy group. More preferably, $R^6$ represents a halogen, especially a chlorine, atom, or a hydroxyl or $C_{1-6}$ alkylcarboxy group. Especially preferred is the case wherein $R^6$ represents a chlorine atom or a hydroxyl or acetoxy group.

In said hydrogenation step, said compound of general formula II is hydrogenated to form a compound of general formula

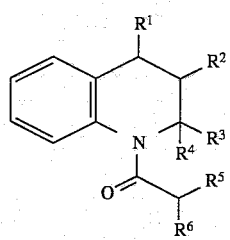

wherein $R^1$, $R^2$, $R^3$, $R^4$, $R^5$ and $R^6$ are as described above.

The reactants and conditions for said hydrogenation step are preferably such as to lead to the predominant formation of a preferred diastereomeric form of said compound of general formula III.

The hydrogenation reaction of said compound of general formula II is preferably carried out in the presence of a heterogenous catalyst. Said heterogenous catalyst preferably includes a transition metal catalyst, a palladium/carbon catalyst being especially preferred.

The hydrogenation reaction is preferably carried out using gaseous hydrogen.

The hydrogenation reaction is preferably carried out in the presence of an organic solvent. Said solvent is preferably polar. Preferred solvents are alcohols or lower alkanoic acids, with methanol and acetic acid being especially preferred.

The hydrogenation reaction is preferably carried out at ambient temperature and pressure. Suitably, a solution comprising said compound of general formula II and said heterogenous catalyst in said organic solvent is stirred in a hydrogen atmosphere over an extended period of time. After the hydrogenation reaction, the catalyst is removed, suitably by filtration, and the compound of general formula III isolated by standard procedures.

Said compound of general formula III is then preferably treated to effect rearrangement and derivatisation, for example, hydrolysis, thereof, in order to prepare the compound of general formula I. The treatment preferably includes slow addition of the compound of general formula III to a strong acid. This initial step may lead to the formation of an intermediate compound of general formula

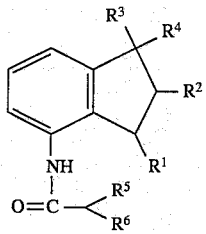

which need not be isolated.

The compound of general formula IV may be hydrolysed by the addition to the reaction mixture of water and a weak acid, for example an alkanoic acid such as acetic acid. The reaction mixture is suitably then heated. The desired compound of general formula I may then be isolated from the reaction mixture by standard procedures.

It will be appreciated that the compound of general formula III described above has at least two chiral atoms, namely the C-4 atom which carries the group $R^1$ and the carbon atom of the group $R^5R^6CH$— and, therefore, the compound may exist in various diastereomeric forms. It has been found that stereoisomeric configurations are generally maintained in the process on going from compounds of general formula III to compounds of general formula I. For example, in a preferred embodiment in which $R^1$, $R^3$ and $R^4$ represent methyl groups, $R^2$ represents a hydrogen atom and $R^5$ and $R^6$ are as described in any statement herein, it has been found that the diasteriomeric purity of the compound of general formula III prepared in the process leads to compounds of general formula I with similar enantiomeric purity.

Also, by using in the process of the first aspect, a compound of general formula II having a group $R^5R^6CH$— of appropriate chirality and by stereoselective hydrogenation of the compound of general formula II, the stereochemistry of the compound of general formula III, and subsequently the compound of general formula I, may be controlled so as to lead to the predominant formation of a preferred stereoisomer. For example, in the preferred embodiment described above in which $R^1$, $R^3$ and $R^4$ represent methyl groups and $R^2$ represents a hydrogen atom, the reaction may be controlled so as to lead to the predominant formation of a preferred enantiomer of the compound of general formula I.

The compound of general formula II may be prepared by reacting a compound of general formula.

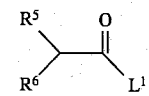

wherein a preferred enantiomer predominates, $R^5$ and $R^6$ are as described above and $L^1$ is a leaving group, with a compound of general formula

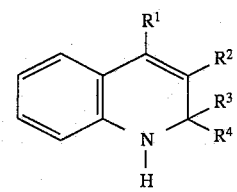

wherein $R^1$, $R^2$, $R^3$ and $R^4$ are as described above.

$L^1$ may represent a halogen atom, especially a chlorine atom, or a hydroxyl, azide, alkoxy, optionally substituted phenoxy, or alkylcarboxy group. Preferably, said compound of general formula V is an anhydride wherein $L^1$ represents a group of general formula

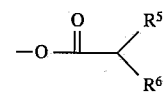

wherein $R^5$ and $R^6$ are as described above; or a group of general formula:

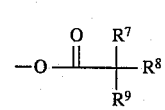

wherein $R^7$, $R^8$ and $R^9$ independently represent a hydrogen atom or an optionally substituted alkyl, alkenyl, alkynyl or phenyl group. Preferably, $R^7$, $R^8$ and $R^9$ represent methyl groups.

In preferred embodiments, said compound of general formula V represents anhydrides of L-(+)-acetoxylactic acid or S-(−)-2-chloropropionic acid. Compounds of general formula V are commercially available and/or may be prepared using standard procedures.

The compound of general formula VI may be prepared using standard procedures.

Said compounds of general formula II, III and IV are believed to be novel and the compounds per se and the processes for the preparation of the compounds constitute further aspects of the present invention.

The compound of general formula I may be reacted with a compound of general formula $$A-\underset{\underset{O}{\|}}{C}-L^2 \quad \text{VII}$$

wherein $L^2$ represents a leaving group and A represents a group of general formula

[structures shown]

wherein X represents a halogen atom, a methyl group or a trifluoromethyl group, Y represents a hydrogen atom, a halogen atom, a lower alkyl group, an amino group, a mercapto group or a lower alkylthio group, $R^{11}$ represents a methyl group or a trifluoromethyl group, and $R^{12}$ and $R^{13}$ independently represent a hydrogen atom or a methyl group to prepare a pesticidal, more particularly a fungicidal, compound of general formula

[structure VIII shown with A—CNH, $R^1$, $R^2$, $R^3$, $R^4$]

Preferably, $L^2$ represents a halogen atom, especially a chlorine atom, or a hydroxyl, azide, alkoxy, optionally substituted phenoxy, alkylcarboxy or alkoxycarboxy group. More preferably, $L^1$ represents an alkoxy group.

Preferably, A represents a group of general formula

[structure with Y, X, S, N]

wherein X and Y are as described above.

More preferably, A represents a group of formula

[structure with N, Me, S]

The reaction of said compounds of general formula I and VII may be carried out in a process analogous to the process described in Japanese Laid-Open Publication No. 92-54173. In the preparation of the compound of general formula VIII, the reactants are preferably mixed together in a solvent. A preferred solvent includes an alcohol and an alkali metal alkoxide, The reaction is preferably carried out at an elevated temperature, suitably at the reflux temperature. The desired product may be isolated using standard procedures.

The invention extends to a compound of general formula I when prepared by the process of the first aspect per se.

According to a second aspect of the present invention, there is provided a process for the preparation of a compound of general formula VIII as described above, the process comprising reacting a compound of general formula I as described above with a compound of general formula VII described above.

The invention extends to a compound of general formula VIII when prepared by the process of the second aspect per se.

In a preferred embodiment, in the compound of general formula I prepared in the process of the first aspect, $R^1$ represents a methyl group, $R^2$ represents a hydrogen atom and $R^3$ and $R^4$ both represent a methyl group. The C-3 atom to which the group $R^1$ is attached is preferably predominantly "R" (rectus) configuration.

The invention will now be described further with reference to the following Examples.

EXAMPLE 1

Preparation of 4-Amino-1,1,3-Trimethylindane[Enriched in 3R-4-Amino-1,1,-3-Trimethylindane Stereoisomer]

[$R^1$=methyl; $R^2$=H; $R^3$=$R^4$=methyl in the compound of general formula I]

A. ROUTE NO. 1

(i) Preparation of 1-(2S-2-Chloropropionyl)- 1,2-Dihydro-2,2,4-Trimethylquinoline

[$R^1$=methyl; $R^2$=hydrogen; $R^3$=$R^4$=methyl; $R^5$=methyl; and $R^6$=chlorine in the compound of general formula II].

To S-(−)-2-chloropropionic acid (10.3 g, 95 mmol.) in tetrahydrofuran (70 ml) was added N,N'-dicyclohexylcarbodiimide (9.83 g, 47.5 mmol) and the mixture stirred at ambient temperature for 1.5 hours. The N,N'-dicyclohexylurea by-product was filtered off and the filtrate concentrated to give the crude anhydride (10.8 g) which was used without further purification. This was mixed with 1,2-dihydro-2,2,4-trimethylquinoline (6.5 g, 37.5 mmol) and heated at 100°–105° C. for 8 hours under a nitrogen atmosphere. After cooling, the products were dissolved in diethyl ether and back-washed (2×5N HCl, then sodium bicarbonate), dried and freed of solvent to give the amide (9.9 g, purity by gas chromatography 89%, yield 89% ).

NMR (CDCl$_3$): δ (ppm) 1.48,1.55,2.05,2.06(3H,s), 1.67(3H,d,J=7Hz), 4.74(1H,q,J=7Hz), 5.52(1H,s), 6.83(1H, bd), 7.1–7.3(3H,m).

Addition of chiral solvating agent [(−)- 2,2,2-trifluoro-1-(9-anthryl)ethanol] showed the material to comprise a 3/1 enantiomer mixture of the 2S/2R isomers respectively.

Mass Spectrometry: M+' 263/265 (3/1).

(ii) Preparation of 1-(2-Chloropropionyl)- 1,2,3,4-Tetrahydro-2,2,4-Trimethylquinoline

[$R^1$=methyl; $R^2$=H; $R^3$=$R^4$=methyl; $R^5$=methyl; and $R^6$=chlorine in the compound of general formula III].

A solution of the compound prepared in A(i) (2 g) in methanol (25 ml) containing 5% Pd/C catalyst (0.2 g) was stirred in a hydrogen atmosphere at ambient temperature and pressure for 15 hours. The catalyst was filtered and the solvent removed to give the tetrahydroquinoline (1.7 g); crude yield 84%.

This product comprised a 15/5/3/1 mixture of the (4R,2S), (4S,2R), (4S,2S) and (4R,2R) isomers respectively as determined by gas chromatography analysis of diastereomer ratio and the enantiomeric purity of the starting material.

NMR (CDCl$_3$); [4R,2S or 4S,2R isomer] δ (ppm): 1.34, 1.54(3H,d,J=Hz), 1.52,1.63(3H,s), 2.72(1H,m), 4.58(1H,q, J=Hz), 6.70(1H,bd), 7.1–7.3(3H,m).

[4S,2S or 4R,2R isomer] δ (ppm): 1.33,1.69(3H,d,J= 7Hz), 1.48,1.67 (3H,s), 2.82(1H,m), 4.75(1H,q,J=7Hz), 7.1–7.3(3H,m).

(iii) Preparation of 4-Amino-1,1,3-Trimethylindane

To 98% sulphuric acid (2 ml) was added the compound prepared in A(ii) (1.7 g) and heated at 50°–60° C. for 30 minutes. After cautious addition of water (2 ml) and acetic acid (0.5 ml), the mixture was refluxed for 3 hours. The aminoindane product was isolated by basification (aq.NH$_3$) and extraction into diethyl ether. Yield 1.1 g. (83% over two steps).

NMR (CDCl$_3$): δ (ppm) 1.24,1.35(3H,s), 1.37(3H,d,J= Hz), 1.65(1H,dd,J=6,12Hz), 2.23(1H,dd,J=9,12Hz), 3.26(1H,m), 3.64(2H,bs), 6.51(1H,d,J=7Hz), 6.62(1H,d,J= 7Hz), 7.06(1H,t,J=7Hz).

Addition of the chiral solvating agent [(–)- 2,2,2-trifluoro- 1-(9-anthryl)ethanol] showed the product comprised a 2/1 mixture of R and S enantiomers respectively, as determined by integration of the highest field methyl signals. (The signal from the R isomer resonates downfield from that of the S isomer).

B. Route No. 2

(i) Preparation of 1-(2S-2-Acetoxypropionyl)- 1,2-Dihydro-2,2,4-Trimethylquinoline

[R$^1$=methyl; R$^2$=H; R$^3$=R$^4$=methyl; R$^5$=methyl; and R$^6$=–OAc, in the compound of general formula II].

To L(+) -acetoxylactic acid (72 g, 0.55 moles) in tetrahydrofuran (500 ml) was added 1,3-dicyclohexylcarbodiimide (DCC, 56 g, 0.27 moles) in tetrahydrofuran (150 ml) at ambient temperature and stirred for 1.5 hours. The solid urea by-product was filtered and the filtrate flashed free of solvent. The 1,2-dihydro- 2,2,4-trimethylquinoline (38 g, 0.22 moles) was added and the mixture heated at 100° C. for 8 hours. The products were partitioned diethyl ether/water and the organic layer back-washed (5N HCl then sodium bicarbonate) dried (MgSO$_4$) and freed of solvent to give the amide (59 g, gas chromatography showed purity 87%, yield 81%) as an oil.

NMR(CDCl$_3$): δ (ppm) 1.22 (3H,d,J=7Hz), 1.25,1.64, 2.02,2.09(3H,s), 5.51(1H,s), 5.64(1H,q,J=7Hz), 7.1–7.3(3H, m), 7.38(1H,bd).

(ii) Preparation of 1-(2-Acetoxypropionyl) - 1,2,3,4-Tetrahydro-2,2,4-Trimethylquinoline

[R$^1$=methyl; R$^2$=H; R$^3$=R$^4$=methyl; R$^5$=methyl; and R$^6$=—OAc in the compound of general formula III].

A mixture of the compound prepared in B(i) (58 g, GC purity 87%, 0.175 moles) in acetic acid (250 ml) containing 5% palladium-on-carbon catalyst (3 g) was hydrogenated at atmospheric pressure and ambient temperature over 8 hours. A total of 3.3 liters of hydrogen was taken up. The catalyst was filtered off and the filtrate stripped of solvent and partitioned between toluene/sodium bicarbonate. Solvent flash left the reduced amide as an oil (57 g, gas chromatography showed purity 91%, yield 100%). NMR/GC analysis showed the presence of diastereomers in a 70/30 ratio.

(major isomer:4R,2S) NMR(CDCl$_3$) δ (ppm) 1.11, 1.33(3H,d,J=7Hz),1.15(1H,t,J=12Hz), 1.46,1.63,2.16(3H, s), 1.85(1H,dd,J=3,12Hz), 2.68(1H,m), 5.62(1H,q,J=7Hz), 7.1–7.3(3H,m), 7.55(1H,m) .

(iii) Preparation of 4-Amino-1,1,3-Trimethylindane

The acetate compound prepared in B(ii) (55 g, GC purity 91% 0 172 moles) was added over 45 minutes to 98% H$_2$SO$_4$ (50 ml) at 25°–60° C. (exotherm). After stirring for a further 30 minutes at 60° C., water (50 ml) containing acetic acid (10 ml) was cautiously added dropwise and the mixture heated at 100° C. for 3 hours. Petrol (60/80 b.p., 100 ml) was added and the mixture basified to pH 9 with 35% aqueous ammonia (150 ml). Separation of the organic layer, drying (MgSO$_4$) and solvent flash gave the desired product (22.6 g, GC purity 92%, yield 69%). NMR analysis using chiral solvating agent[(–)-2,2,2-trifluoro-1-(9-anthryl)ethanol] showed a 70/30 mixture of enantiomers in favour of the (–)-isomer.

EXAMPLE 2

Preparation of 4-Methyl-N-(1,1,3-Trimethylindan- 4-yl)Thiazole-5-Carboxamide [Enriched in the 4-Methyl-N-(3R-1,1,3-Trimethylindan,4-yl)Thiazole- 5-Carboxamide Stereoisomer]

This compound may be prepared by reaching 4-amino- 1,1,3-trimethylindane prepared in Example 1 with 4-methylthiazole-5-carboxylic acid chloride under conditions analogous to the conditions described in Japanese Laid- Open Publication No. 92-54173.

EXAMPLE 3

Pesticidal Activity

The compound prepared in Example 2 has been found to be fungicidal. Additionally, the fungicidal activity of the 3R enantiomer has been found to be greater than that of the corresponding 3S enantiomer.

I claim:

1. A process for the preparation of an indanylamine compound of formula

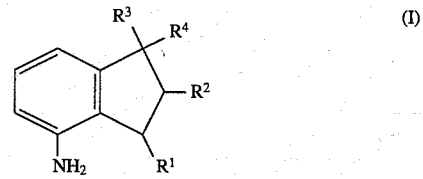

wherein R$^1$ represents an optionally substituted alkyl group, and R$^2$, R$^3$ and R$^4$ independently represent a hydrogen atom or an optionally substituted alkyl group, the process comprising hydrogenating a compound of formula

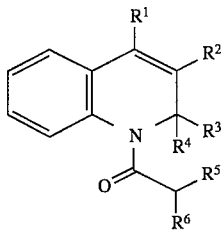
(II)

wherein $R^1$, $R^2$, $R^3$ and $R^4$ are as described above, and $R^5$ and $R^6$ independently represent a halogen atom, a hydroxyl, nitro or cyano group, or an optionally substituted alkyl, alkoxy, alkoxycarbonyl, alkylcarboxy or alkylamino group, provided that $R^5$ and $R^6$ represent different atoms or groups, to form a first intermediate compound of formula

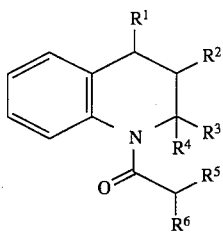
(III)

wherein $R^1$ to $R^6$ are as described above:

rearranging the first intermediate compound of formula III with a strong acid to form a second intermediate compound of formula

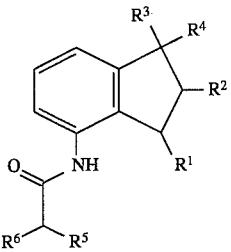
(IV)

wherein $R^1$ to $R^6$ are as described above: and hydrolyzing the second intermediate compound of formula IV with a weak acid in the presence of water.

2. The process according to claim 1, wherein $R^1$, $R^3$ and $R^4$ represent a methyl group and $R^2$ represents a hydrogen atom.

3. The process according to claim 2 wherein $R^5$ represents a $C_{1-6}$ alkyl group and $R^6$ represents a chlorine atom, or a hydroxyl or $C_{1-6}$ alkylcarboxy group.

4. A process for the preparation of an intermediate compound of formula

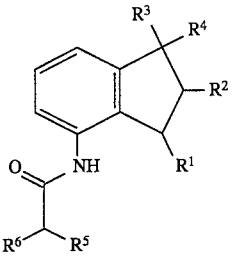
(IV)

wherein $R_1$ represents an optionally substituted alkyl group, $R^2 R^3$ and $R^4$ independently represent a hydrogen atom or an optionally substituted alkyl group, and $R^5$ and $R^6$ independently represent a halogen atom, a hydroxyl, nitro or cyano group, or an optionally substituted alkyl, alkoxy, alkoxycarbonyl, alkylcarboxy or alkylamino group, provided that $R^5$ and $R^6$ represent different atoms or groups, which comprises rearranging an intermediate compound of formula

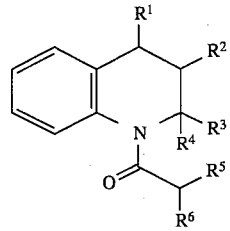
(III)

wherein $R^1$ to $R^6$ are as described above, with a strong acid.

5. A process for the preparation of a compound of formula

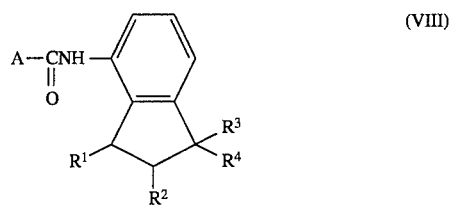
(VIII)

wherein A represents a group selected from the group consisting of

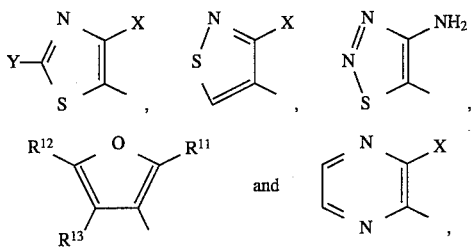

and wherein X represents a halogen atom, a methyl group or a trifluoromethyl group, Y represents a hydrogen atom, a halogen atom, a lower alkyl group, an amino group, a mercapto group or a lower alkylthio group, $R^{11}$ represents a methyl group or a trifluoromethyl group, $R^{12}$ and $R^{13}$ independently represent a hydrogen atom or a methyl group, $R^1$ represents an optionally substituted alkyl group, and $R^2$, $R^3$ and $R^4$ independently represent a hydrogen atom or an optionally substituted alkyl group, which comprises the steps of (a) hydrogenating a compound of formula

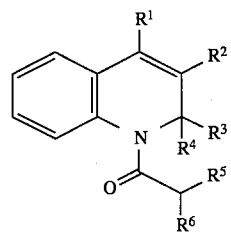
(II)

wherein $R^1$, $R^2$, $R^3$ and $R^4$ are as described above and $R^5$ and $R^6$ independently represent a halogen atom, a hydroxyl, nitro or cyano group, or an optionally substituted alkyl, alkoxy, alkylcarbonyl, alkylcarboxy or alkylamino group provided that $R^5$ and $R^6$ represent different atoms or groups to form a first intermediate compound of formula

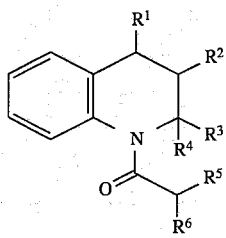

wherein $R^1$ to $R^6$ are as described above;

(b) rearranging the first intermediate compound of formula III with a strong acid to form a second intermediate compound of formula

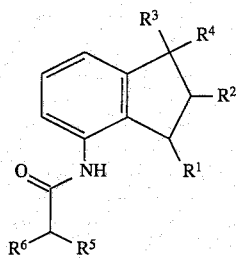

wherein $R^1$ to $R^6$ are as described above;

(c) hydrolyzing the second intermediate compound of formula IV with a weak acid in the presence of water to form an indanylamine compound of formula

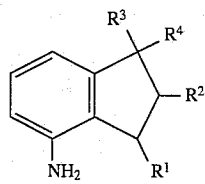

wherein $R^1$ to $R^4$ are as described above; and (d) reacting the indanylamine compound of formula I with a compound of formula

wherein A is as described above and $L^2$ represents a halogen atom, or a hydroxyl, azide, alkoxy, optionally substituted phenoxy, alkylcarboxy or alkoxycarboxy group.

6. The process according to claim 5, wherein A is

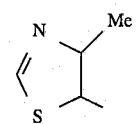

in said compound of general formula VIII.

* * * * *

UNITED STATES PATENT AND TRADEMARK OFFICE
CERTIFICATE OF CORRECTION

PATENT NO. : 5,521,317
DATED : May 28, 1996
INVENTOR(S) : Paul H. Briner

It is certified that error appears in the above-identified patent and that said Letters Patent is hereby corrected as shown below:

Title page, item [73], Assignee: should read --Shell Research Limited

Signed and Sealed this

Twenty-ninth Day of August, 2000

Attest:

Q. TODD DICKINSON

*Attesting Officer*     *Director of Patents and Trademarks*